United States Patent [19]

Shinohara et al.

[11] Patent Number: 4,965,387

[45] Date of Patent: Oct. 23, 1990

[54] TRIORGANOSILYLMETHYL ESTERS OF α-TRIFLUOROMETHYLACRYLIC ACID

[75] Inventors: Toshio Shinohara, Takasaki; Masatoshi Hayashi, Fukui, both of Japan

[73] Assignee: Shin-Etsu Chemical Co., Ltd., Tokyo, Japan

[21] Appl. No.: 497,165

[22] Filed: Mar. 22, 1990

[30] Foreign Application Priority Data

Mar. 24, 1989 [JP] Japan ................................. 1-72343

[51] Int. Cl.$^5$ ............................................... C07F 7/08
[52] U.S. Cl. ................................................... 556/440
[58] Field of Search ....................................... 556/440

[56] References Cited

U.S. PATENT DOCUMENTS 4,503,208  3/1985  Lin et al. ........................ 556/440 X
4,558,111  12/1985  Tolentino ....................... 556/440 X

OTHER PUBLICATIONS

Journal of Organic Chemistry, Dec. 1956, pp. 1537–1539.

*Primary Examiner*—Paul F. Shaver
*Attorney, Agent, or Firm*—Lowe, Price, LeBlanc, Becker & Shur

[57]  ABSTRACT

A novel organosilicon compound of the following formula

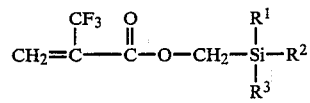

wherein $R^1$, $R^2$ and $R^3$, respectively, represent a monovalent hydrocarbon group having from 1 to 8 carbon atoms, is described.

2 Claims, 1 Drawing Sheet

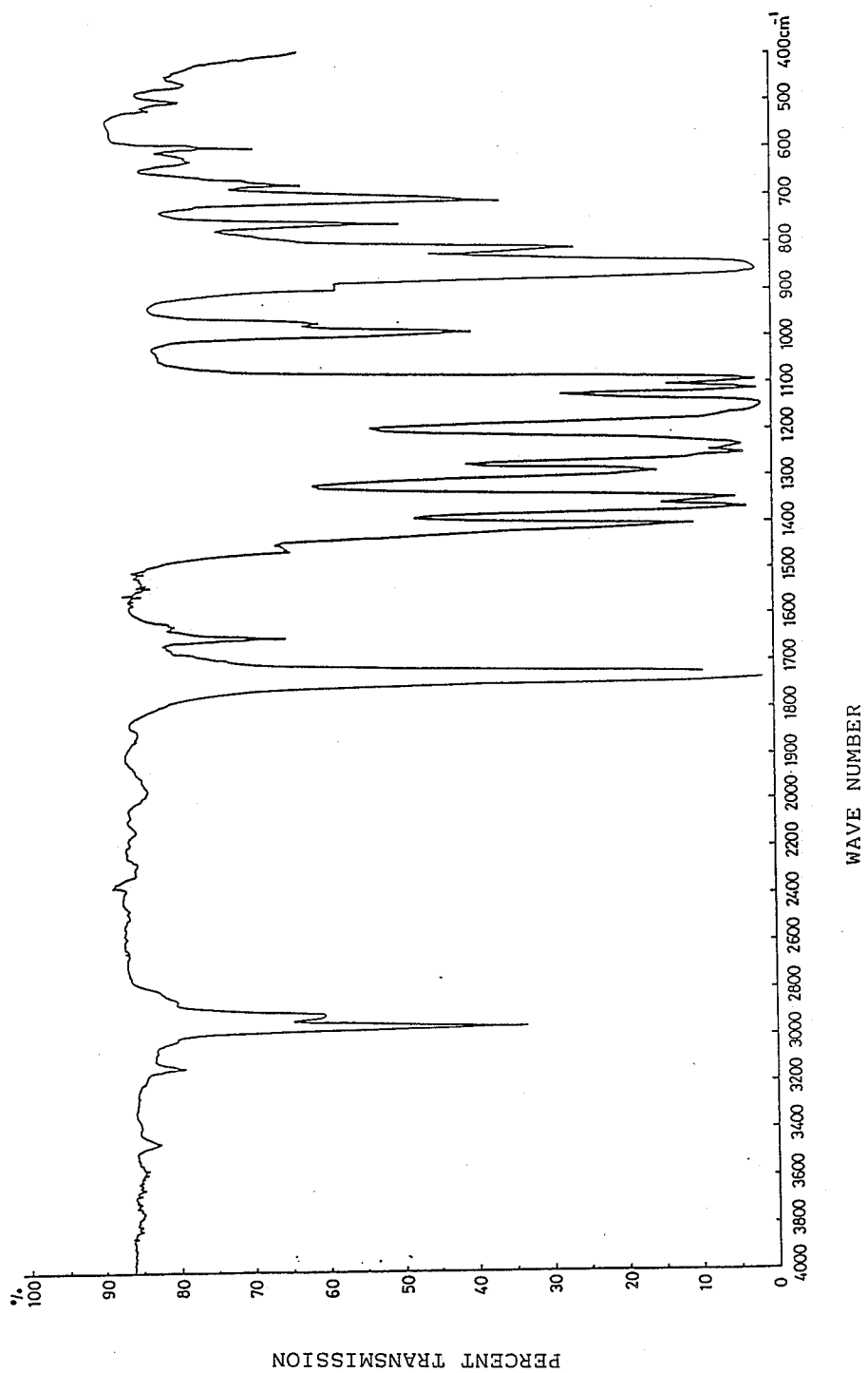

TRIORGANOSILYLMETHYL ESTERS OF α-TRIFLUOROMETHYLACRYLIC ACID

BACKGROUND OF THE INVENTION

1. Field of the Invention

This invention relates to novel organosilicon compounds and more particularly, to novel triorganosilylmethyl esters of α-trifluoromethylacrylic acid.

Description of The Prior Art

Methacryloxymethyltrimethylsilane of the formula,

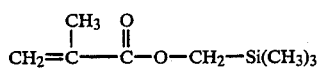

is known in the art (Journal of Organic Chemistry, 21, 1537 (1956)). Studies have been made on this compound wherein the compound is copolymerized with methyl methacrylate and utilized as hard contact lenses. However, the copolymer has a low oxygen permeability. A recent trend for contact lenses requires a high oxygen permeability and the copolymer is not satisfactory in this regard.

SUMMARY OF THE INVENTION

It is accordingly an object of the invention to provide a novel organosilicon compound which has wide utility as an intermediate useful for preparation of various compounds.

It is another object of the invention to provide novel triorganosilylmethyl esters of α-trifluoromethylacrylic acid which have wide utility in various fields and are particularly useful as transparent optics after copolymerization with co-monomers such as methyl methacrylate.

The above objects can be achieved, according to the invention, by a novel organosilicon compound of the following general formula

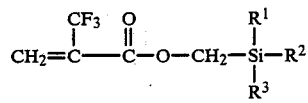

wherein $R^1$, $R^2$ and $R^3$, respectively, represent a monovalent hydrocarbon group having from 1 to 8 carbon atoms.

BRIEF DESCRIPTION OF THE DRAWING

The sole FIGURE is an IR spectrum chart of a compound obtained in Example 1.

DETAILED DESCRIPTION AND EMBODIMENTS OF THE INVENTION

In the above-defined formula for the novel organosilicon compound, $R^1$, $R^2$ and $R^3$, independently, represent a monovalent hydrocarbon having from 1 to 8 carbon atoms. Examples of the monovalent hydrocarbon include a saturated or unsaturated linear or branched aliphatic hydrocarbon group such as a methyl group, an ethyl group, a propyl group, a butyl group, a vinyl group, an allyl group, and aromatic groups such as a phenyl group. Of these, a methyl group is preferred for each substituent.

The compound of the invention can be prepared, for example, by reaction between α-trifluoromethylacrylic acid and trimethylsilyl methanol in the presence of a strong acid. Examples of the strong acid catalyst include sulfuric acid, hydrochloric acid, $CF_3COOH$, $CF_3SO_3H$ and the like. The catalyst is generally used in an amount of from $1 \times 10^{-6}$ to $1 \times 10^{-2}$ mole per mole of the starting α-trifluoromethylacrylic acid. The reaction temperature is in the range of from 30° to 150° C., preferably from 30° to 150° C. and the reaction time is in the range of from 0.5 to 30 hours.

The present invention is described by way of example.

EXAMPLE 42.0 g (0.3 moles) of α-trifluoromethylacrylic acid, 34.4 g (0.33 moles) of trimethylsilyl methanol and 0.1 g of trifluoromethanesulfonic acid were charged into a reactor and heated at a temperature of 100° to 120° C. for 2 hours. After completion of the reaction, secondarily produced water was separated from the reaction system and the resultant organic phase was neutralized with a sodium hydrogencarbonate aqueous solution, followed by drying with sodium sulfate and distillation under reduced pressure to obtain 59 g of a liquid having a boiling point of 93° to 94° C./81 mmHg. This liquid was subjected to gas chromatographic analysis, revealing that it consisted of a single ingredient. The liquid was further subjected to measurement of the molecular weight, elementary analysis and NMR and IR analyses. The results are shown below.

Molecular weight (by gas chromatographic mass spectrometry): 226

|  | Elementary analysis: | | |
|---|---|---|---|
|  | Si(%) | C(%) | H(%) |
| Calculated | 12.41 | 42.47 | 5.79 |
| Found | 12.45 | 42.43 | 5.81 |

NMR analysis δ (ppm): 0.11 (s, 9H, Si-CH$_3$), 3.93 (s, 2H, O—CH$_2$—Si), 6.50 (q, 2H, C=CH$_2$).

IR analysis: shown in FIG. 1.

From the above results, the liquid was confirmed to be trimethylsilylmethyl ester of α-trifluoromethylacrylic acid of the following structural formula. The yield was 87%.

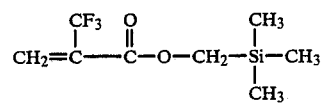

REFERENCE

The trimethylsilylmethyl ester of α-trifluoromethylacrylic acid obtained in Example and methyl methacrylate were charged at equimolar amounts, to which benzoyl peroxide was added, followed by keeping at a temperature of 100° C. and allowing to stand. One hour after the standing, a solid polymer was obtained (copolymer A).

Methacryloxymethyltrimethylsilane of the following formula

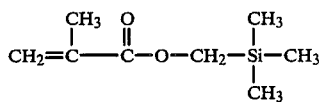

which is described in J. Org. Chem., 21, 1537 (1956), were treated in the same manner as in Example, thereby obtaining a polymer (copolymer B).

The two copolymers were subjected to measurement of oxygen permeability with the result that the oxygen permeability of the copolymer A was 1.6 times as high as than of the copolymer B.

What is claimed is:

1. An organosilicon compound of the following formula

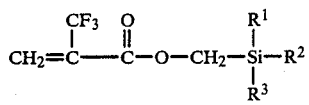

wherein $R^1$, $R^2$ and $R^3$, respectively, represent a monovalent hydrocarbon group having from 1 to 8 carbon atoms.

2. An organosilicon compound according to claim 1, wherein $R^1$, $R^2$ and $R^3$, respectively, represent a methyl group.

* * * * *